United States Patent [19]

Metz et al.

[11] Patent Number: 4,855,517
[45] Date of Patent: Aug. 8, 1989

[54] PROCESS FOR PREPARING AROMATIC BROMINE COMPOUNDS

[75] Inventors: Hans J. Metz, Heppenheim; Klaus Warning, Eppstein/Taunus, both of Fed. Rep. of Germany

[73] Assignee: Hoechst Aktiengesellschaft, Frankfurt am Main, Fed. Rep. of Germany

[21] Appl. No.: 98,717

[22] Filed: Sep. 21, 1987

Related U.S. Application Data

[63] Continuation of Ser. No. 770,409, Aug. 28, 1985.

[30] Foreign Application Priority Data

Aug. 30, 1984 [DE] Fed. Rep. of Germany ....... 3431826

[51] Int. Cl.$^4$ .................. C07C 21/24; C07C 17/12
[52] U.S. Cl. ................................. 570/206; 570/191; 570/144; 570/147; 560/8; 562/493
[58] Field of Search ............... 570/206, 191, 144, 147; 560/8; 562/493; 260/465 G

[56] References Cited

U.S. PATENT DOCUMENTS

| 3,499,046 | 3/1970 | Wall et al. | 570/147 |
| 3,732,321 | 5/1973 | Raley | 558/425 |
| 4,543,214 | 9/1985 | Somlo et al. | 260/694 |
| 4,582,948 | 4/1986 | Tang et al. | 570/144 |

FOREIGN PATENT DOCUMENTS

| 12375523 | 3/1968 | Fed. Rep. of Germany | 570/206 |
| 2256167 | 4/1974 | Fed. Rep. of Germany | 570/206 |
| 1419180 | 12/1975 | United Kingdom | 570/206 |

OTHER PUBLICATIONS

Dhar, "J. Chem. Soc.", vol. 117, pp. 993 (1920).
S. N. Dhar, J. Chem. Soc. (1920), 117, 993.
*Hackh's Chemical Dictionary*, 3rd Ed., McGraw-Hill Book Company, Inc. at p. 395.
*Organic Chemistry*, 3rd Ed. by Morrison & Boyd, Allyn and Bacon, Inc. at p. 45.

Primary Examiner—Werren B. Lone
Attorney, Agent, or Firm—Curtis, Morris & Safford

[57] ABSTRACT

Aromatic bromine compounds are prepared by reacting aromatic nitro compounds with elemental bromine in the gas phase at temperatures between about 310° to 550° C. In this reaction, the nitro groups are selectively replaced by bromine; further bromination of the aromatic system beyond that does not take place.

14 Claims, No Drawings

PROCESS FOR PREPARING AROMATIC BROMINE COMPOUNDS

This application is a continuation of application Ser. No. 770,409, filed Aug. 28, 1985.

Aromatic bromine compounds such as, for example, bromobenzene or 3,5-dibromobenzoic acid, are primarily useful intermediates in various fields such as dyes, polymers and pharmaceuticals.

They can be prepared by various known processes. A customary and frequently employed process is ring bromination of aromatic compounds, but this method virtually always except for the case of the monobromination of (unsubstituted) benzene—produces isomeric mixtures. The individual isomers are frequently very difficult to separate. Certain, especially poly-ring-brominated aromatics are virtually impossible to prepare economically by this process, due to the directing action of existing substituents. In such cases the so-called Sandmeyer reaction is frequently chosen as an indirect pathway.

The starting materials in the Sandmeyer reaction are aromatic amines or aromatic nitro compounds which are reduced to amines. In either case the amine is then converted into the corresponding diazonium salt, which is finally converted in a further stage with a bromide under the catalytic action of copper(I) ions into the desired bromine derivative. The multistage procedure and the fact that copper-containing effluents need to be treated lead to considerable production costs.

A further, comparatively unconsidered way of preparing aromatic bromine compounds consists in the direct replacement of the nitro groups of aromatic nitro compounds by elemental bromine (S.N. Dhar, J. Chem. Soc. (1920), 117, 993). The process operates in general at temperatures of up to about 250° C.—in special individual cases up to a maximum of 300° C.—in a closed system, i.e. surely predominantly in liquid phase. However, with this process it is practically not possible to obtain selective replacement by bromine of only the nitro groups present in the aromatic starting nitro compounds without also substantially replacing the aromatically bonded hydrogen atoms still present. For that reason the end products of the reaction are generally polybrominated products, i.e. aromatic bromine compounds which have more bromine substituents than they previously had nitro groups. The reason for the degree of bromination beyond the replacement of the nitro groups present is said to be the formation of a reactive Br-containing intermediate (NO$_2$Br) which readily undergoes reaction with still free (unsubstituted) positions of the aromatic system in the course of which the hydrogen atoms are replaced by bromine, for example:

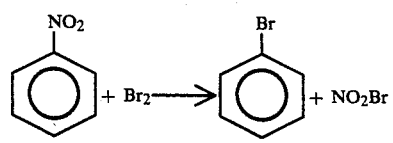

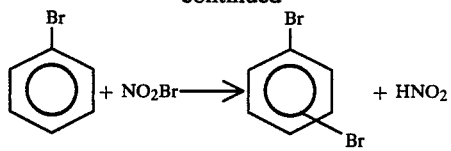

Because of the usually undesirable excess bromination of the aromatic nitro compounds beyond the mere replacement of the nitro groups it is the object of the present invention to modify the known process in such a way that no further bromination takes place any longer beyond the replacement of the nitro groups present.

This object can be achieved according to the invention by carrying out the reaction in the gas phase at temperatures between about 310° and 550° C.

The invention accordingly provides a process for preparing aromatic bromine compounds by reacting aromatic nitro compounds with elemental bromine at elevated temperature, which comprises carrying out the reaction in the gas phase at temperatures between about 310° and 550° C.

In this process, a bromine substituent is only introduced in those positions of the molecule to which previously a nitro group was bonded. That is extremely surprising, since it had to be assumed, in particular owing to the mechanism postulated by Dhar Loc. cit. for the known reaction (via the reactive intermediate NO$_2$Br), that the reactive intermediate NO$_2$Br is formed independently of the reaction conditions and that the aromatic starting nitro compounds are invariably brominated to a degree which goes beyond the replacement of the existing nitro groups by bromine.

The starting compounds for the process according to the invention can in principle be any possible aromatic nitro compound; however, owing to the reduced danger of decomposition on conversion into the gas phase, preference is given to the use of mononitrobenzene or dinitrobenzene which may be substituted by inert groups. Particularly preferred starting compounds are the compounds of the formula I

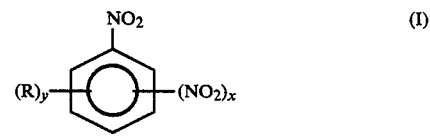

in which

R = halogen,
  trihalogenomethyl,
  COOH,
  CN,
  COOR' (R' = lower alkyl),
  COCl,
  COBr,
  CONR"$_2$ (R" = hydrogen or lower alkyl);
  OC$_6$H$_5$,
  OC$_n$F$_{2n+1}$ (n = integer from 1-3),
  NCO
x = 0 or 1, and
y = 0 or an integer from 1-5
  (if x = 0) or
  = 0 or an integer from 1-4
  (if x = 1).

Very particular preference is given to those compounds of the formula I in which

| | |
|---|---|
| R = | F, Cl, |
| | CF$_3$, CCl$_3$, |
| | COOH, |
| | CN, |
| | COCl, COBr, |
| x = | 0 or 1 and |
| y = | 0 or 1. |

Examples of starting compounds which fall within the formula I are:

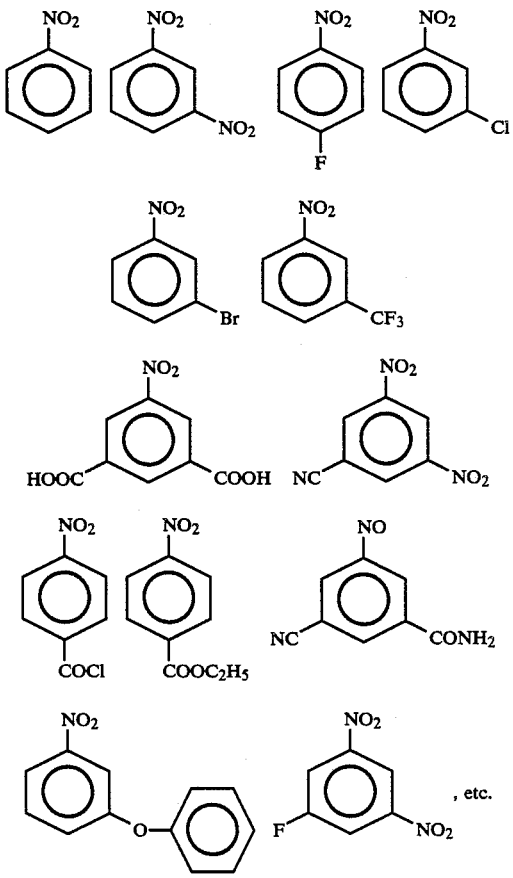

The compounds can be prepared by known methods.

The molar ratio of aromatic starting nitro compound: elemental bromine is not especially critical; however, preference is given to the use of about ½ to 1 mol of elemental bromine per mol of nitro groups present in the aromatic nitro compounds. The bromine can be as required pure or be used in the reaction in the form of a mixture with an inert gas (for example nitrogen, argon, etc.).

To carry out the process, the aromatic nitro compound is evaporated and is contacted in the gas phase with bromine vapors at the abovementioned temperatures (between about 310° and 550° C.). The evaporation of the aromatic nitro compounds can—depending on their stability and technical circumstances—be carried out under reduced, elevated or atmospheric pressure, the specific evaporation temperature having to be chosen in the known manner in accordance with the specific set pressure. Atmospheric pressure is the preferred pressure.

The evaporation can be supported by addition of an inert gas which serves as an entrainer. The evaporated aromatic nitro compound is subsequently mixed with the bromine vapors and reacted therewith at the desired temperature within the specified range. The optimal reaction temperature depends on the nature of the aromatic nitro compound used and may be determined by simple preliminary experiments.

The process can be carried out for example in a flow pipe operating under steady state conditions in which the evaporated aromatic nitro compound is heated to the respective reaction temperature together with the desired amount of bromine. It is possible to carry out the reaction within the entire pressure range in which the reaction mixture is still gaseous at the respective temperature. The optimal residence times are normally within the range of from about 20 to 400 seconds and may be determined together with the optimal reaction temperature in simple preliminary experiments. The reaction mixtures obtained are advantageously separated into the components either only by rectification or by washing out the inorganic byproducts for example with sulfite/carbonate solution or an alkali metal hydroxide solution, and by downstream rectification of the organic products.

Unreacted starting material is reused after it has been separated off, preferably by distillation.

Owing to the opening up of the possibility of the selective and controlled replacement of nitro groups in aromatic nitro compounds by bromine without further substitution by bromine beyond that extent the invention constitutes a significant enrichment of the art in the field of the preparation of bromine-containing aromatics.

The invention will now be illustrated in more detail by the following Examples.

EXAMPLES

1. Preparation of 4-bromofluorobenzene 141 g (=1 mol) of 4-fluoronitrobenzene were evaporated at 200°–240° C. and the vapor was passed together with 128 g (=0.8 mol) of bromine (molar ratio 1:0.8) through a flow pipe (dimensions: $\theta$=30 mm, liter=600 mm) in the course of 4 hours, during which the gas stream was heated to a final temperature of 400° C. The organic portion of the product mixture had the following composition (GC analysis):

| | |
|---|---|
| 4-Bromofluorobenzene | 62% |
| 4-Fluoronitrobenzene | 35% |
| Byproducts | 3% |

The yield of 4-bromofluorobenzene, relative to reacted 4-fluoronitrobenzene, was accordingly 85.5% of theory.

2. Preparation of 1,3-dibromobenzene 200 g (=0.99 mol) of 3-bromonitrobenzene and 126 g (=0.78 mol) of bromine (molar ratio 1:0.8) were evaporated together and passed at T$_{max}$=420° C. through a flow pipe for 4 hours. The mixture of the organic reaction products had the following composition (GC analysis):

| | |
|---|---|
| 1,3-Dibromobenzene | 77% |

-continued

| | |
|---|---|
| 3-Bromonitrobenzene | 16% |
| Byproducts | 7% |

The yield of 1,3-dibromobenzene, relative to reacted 3-bromonitrobenzene, was accordingly 85.6% of theory.

3. Preparation of 1,3-dibromobenzene and 3-bromonitrobenzene 104 g (=0.62 mol) of 1,3-dinitrobenzene were evaporated together with 120 g (=0.75 mol) of bromine in a stream of nitrogen (5 liters/h) and passed at $T_{max} = 350°$ C. through a flow pipe for 3 hours. The product mixture obtained had the following composition (GC analysis):

| | |
|---|---|
| 1,3-Dibromobenzene | 28% |
| 3-Bromonitrobenzene | 31% |
| 1,3-Dinitrobenzene | 39% |
| Byproducts | 2% |

The yield of 1,3-dibromobenzene, relative to reacted 1,3-dinitrobenzene, was accordingly 45.9% of theory. The yield of 3-bromonitrobenzene, relative to reacted 1,3-dinitrobenzene, was 50.8% of theory.

We claim:

1. A process for preparing an aromatic bromine compound which comprises reacting an aromatic nitro compound of the formula I

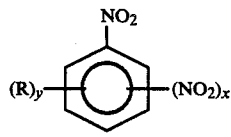

in which R is F, Cl, Br,
trifluoromethyl,
CN,
COBr,
$OC_6H_5$,
$OC_nF_{2n+1}$, where n is an integer from 1-3,
or NCO,
x is 0 or 1, and
y is 0 or 1 with elemental bromine in the gas phase at a temperature between about 310° and 550° C. to produce the exclusive replacement of at least one of the nitro groups with a bromine atom.

2. The process as claimed in claim 1, wherein the mononuclear aromatic nitro compound used is a compound of the formula I where
R is F, Cl, Br,
$CF_3$,
CN, or
COBr,
x is 0 or 1 and
y is 0 or 1.

3. The process as claimed in claim 1, wherein the vaporized aromatic nitro compound is conducted with bromine through a flow pipe which is heated to at least 310° C.

4. The process as claimed in claim 3, wherein the residence time of the gaseous mixture is in the range of from about 20 to 400 seconds.

5. The process as claimed in claim 1, wherein the aromatic nitro compound used is mononitrobenzene or dinitrobenzene.

6. A process for preparing a aromatic bromine compound by reacting a mononuclear aromatic compound containing a plurality of nitro groups with elemental bromine at elevated temperature which comprises carrying out the reaction in the gas phase at temperatures between about 310° C. and 550° C. to produce the selective and controlled replacement of at least one of the nitro groups with a bromine atom.

7. The process of claim 6 wherein about ½ to 1 mol of elemental bromine is used per mol of nitro groups in the starting mononuclear aromatic compounds containing a plurality of nitro groups.

8. A process for preparing a mononuclear aromatic bromine compound by reacting elemental bromine with a mononuclear aromatic compound containing a plurality of nitro groups and which may be further unsubstituted or substituted with non-nitro groups which are inert to replacement by bromine which comprises carrying out the reaction in the gas phase at temperatures between about 310° C. and 550° C. to produce the selective and controlled replacement of at least one of the nitro groups with a bromine atom.

9. A process for preparing an aromatic bromine compound by reacting a compound of the formula I

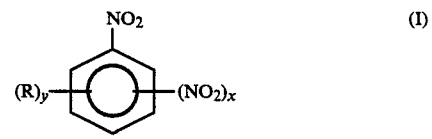

in which R is F, Cl, Br,
trifluoromethyl,
CN,
COBr,
$OC_6H_5$,
$OC_nF_{2n+1}$, where n is an integer from 1-3,
or
NCO,
x is 0 or 1, and
y is 0 or 1
with elemental bromine at elevated temperature which comprises carrying out the reaction in the gas phase at temperatures between about 310° C. and 550° C. to produce a compound of the formula II

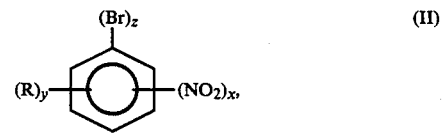

in which R and y are as defined above,
x' is x, when x is 0,
x' is 0 or 1, when x is 1, and
z is x'+1.

10. The process of claim 9 wherein the amount of elemental bromine used is from 0.5 (x+1) mol to (x+1) mol.

11. The process of claim 9 wherein in the compounds of formulas I and II
R is F, Cl, Br
$CF_3$, CN,
or COBr.

12. A process for preparing a mononuclear aromatic bromine compound by reacting a mononuclear aromatic compound containing a plurality of nitro groups with elemental bromine at elevated temperature which comprises carrying out the reaction in the gas phase at temperatures between about 310° C. and 550° C. to produce the selective and controlled replacement of each of the nitro groups with a bromine atom.

13. A process for preparing a mononuclear aromatic bromine compound by reacting a mononuclear aromatic compound containing at least one nitro group, which is unsubstituted or substituted with at least one non-nitro group which is inert to replacement by bromine with elemental bromine at elevated temperature which comprises carrying out the reaction in the gas phase at temperatures between about 310° C. and 550° C. to produce the exclusive replacement of at least one nitro group with bromine.

14. A process for preparing a mononuclear aromatic bromine compound which comprises reacting a mononuclear aromatic nitro compound containing at least one nitro group with elemental bromine in the gas phase at a temperature between about 310 and 550° C. to produce the exclusive replacement of at least one of the nitro groups with a bromine atom, the bromine being used in an amount of about ½ to 1 mole of bromine per mole of nitro groups in the monocyclic aromatic starting nitro compounds.

* * * * *

UNITED STATES PATENT AND TRADEMARK OFFICE
CERTIFICATE OF CORRECTION

PATENT NO. : 4,855,517
DATED : August 8, 1989
INVENTOR(S) : Metz et al.

It is certified that error appears in the above-identified patent and that said Letters Patent is hereby corrected as shown below:

1. Claim 6, line 1, before "aromatic" insert --mononuclear--.

2. Please add Claim 15 as follows:

--15. A process for preparing a mononuclear aromatic bromine compound by reacting a mononuclear aromatic compound containing at least one nitro group, which is unsubstituted or substituted with at least one non-nitro group which is inert to replacement by bromine with elemental bromine at elevated temperature which comprises carrying out the reaction in the gas phase at temperatures between about 350°C and 420°C to produce the exclusive replacement of at least one nitro group with bromine.--

Signed and Sealed this

Twenty-eighth Day of August, 1990

Attest:

HARRY F. MANBECK, JR.

*Attesting Officer*  *Commissioner of Patents and Trademarks*